(12) United States Patent
Kikuchi

(10) Patent No.: US 6,385,289 B1
(45) Date of Patent: May 7, 2002

(54) X-RAY DIFFRACTION APPARATUS AND METHOD FOR MEASURING X-RAY ROCKING CURVES

(75) Inventor: Tetsuo Kikuchi, Tachikawa (JP)

(73) Assignee: Rigaku Corporation, Tokyo (JP)

( * ) Notice: Subject to any disclaimer, the term of this patent is extended or adjusted under 35 U.S.C. 154(b) by 0 days.

(21) Appl. No.: 09/546,890

(22) Filed: Apr. 10, 2000

(30) Foreign Application Priority Data

Apr. 12, 1999 (JP) ........................................... 11-104476

(51) Int. Cl.[7] ............................................... G01N 13/00
(52) U.S. Cl. ............................ 378/79; 378/70; 378/71; 378/79
(58) Field of Search .............................. 378/70, 71, 79

(56) References Cited

U.S. PATENT DOCUMENTS

| | | | | |
|---|---|---|---|---|
| 5,446,777 A | * | 8/1995 | Houtman | 378/45 |
| 5,568,531 A | * | 10/1996 | Nishihagi et al. | 378/71 |
| 5,926,720 A | * | 7/1999 | Barton et al. | 378/84 |

FOREIGN PATENT DOCUMENTS

DE 0553911 A1 * 8/1993 ........................ 23/20

OTHER PUBLICATIONS

"X-ray Diffusion, Experimental Physics Course", vol. 20, edited by Kazutake Kohra, p. 477, issued by Kyoritsu Shuppan, Japan, 1988.

* cited by examiner

*Primary Examiner*—Robert H. Kim
*Assistant Examiner*—Therese Barber
(74) *Attorney, Agent, or Firm*—Frishauf, Holtz, Goodman, Langer & Chick, P.C.

(57) ABSTRACT

A two-dimensional position-sensitive X-ray detector is used for the precision measurement of lattice constants so that a plurality of X-ray rocking curves can be measured at the same time for the respective points on a sample and an area map, on the sample, of the lattice constants can be obtained in a short time. X-rays from an X-ray source pass through the first slit and are then incident on a crystal collimator. X-rays reflected by the crystal collimator are incident on the sample. X-rays diffracted at the sample are detected by the two-dimensional position-sensitive X-ray detector. The diffracted X-rays from the respective points on the sample are detected separately at respective points on the X-ray detector. X-ray intensities which are detected at respective points on the detecting surface of the X-ray detector are recorded, at the same time, at every rotation angle with a predetermined pitch of angle during sample rotation, so that a plurality of rocking curves for said respective points of the sample can be obtained at the same time.

11 Claims, 14 Drawing Sheets

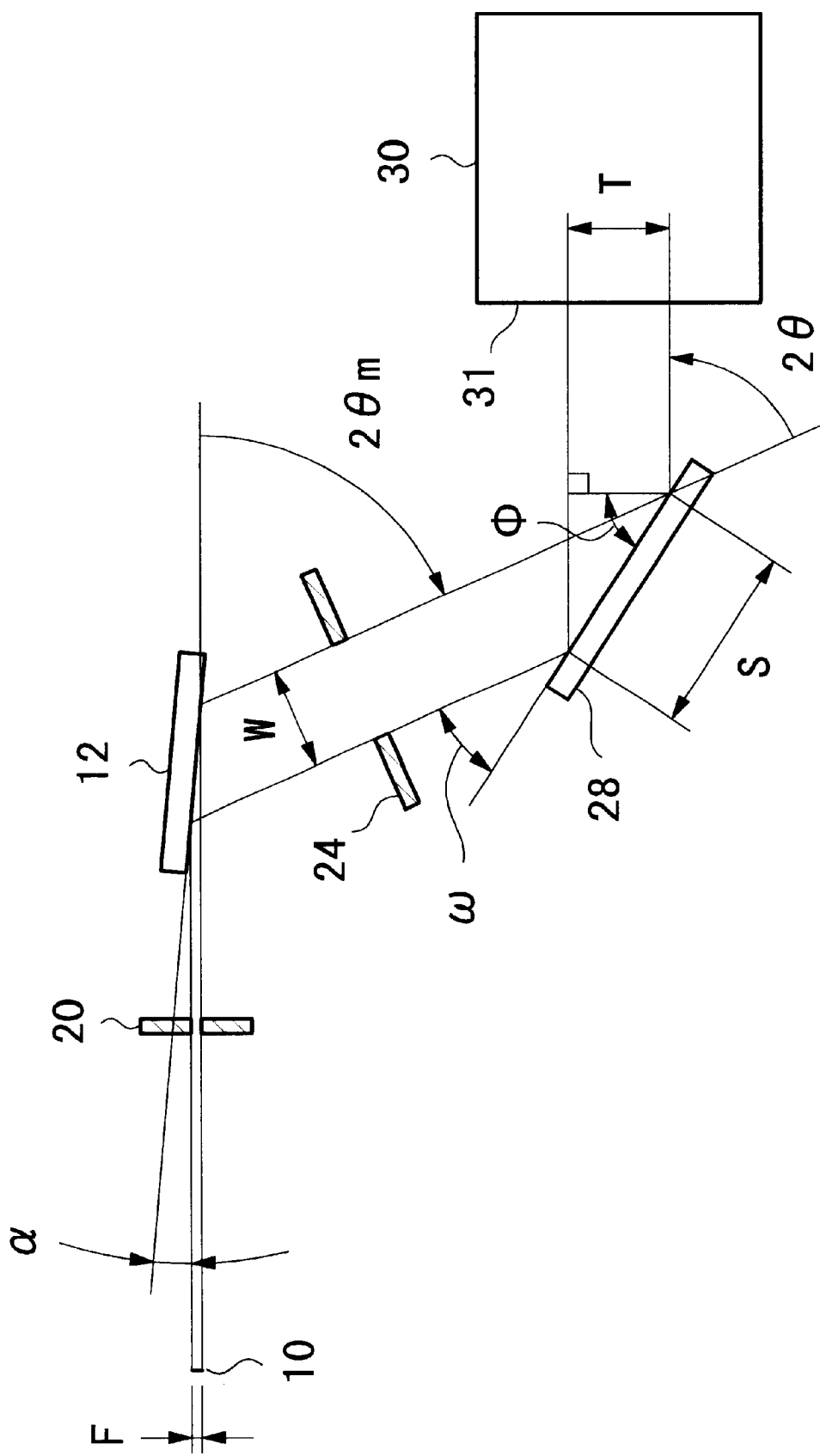

ROTATION ANGLE $\omega$

X-RAY DIFFRACTION APPARATUS AND METHOD FOR MEASURING X-RAY ROCKING CURVES

BACKGROUND OF THE INVENTION

This invention relates to X-ray diffraction apparatus for measuring in-plane distribution of the interplanar spacing of the crystal lattice of an epitaxial thin film deposited on a single crystal substrate and a method for measuring X-ray rocking curves.

An X-ray rocking curve measurement using X-ray diffraction has often been used for measuring the lattice constants of a single-crystal thin film which is epitaxially deposited on a single crystal substrate. The crystal lattice constants can be calculated by using Miller indices and its interplanar spacing. In the X-ray rocking curve measurement, a diffraction peak angle is precisely measured so that the interplanar spacing can be calculated. The resulting interplanar spacing is used to determine the lattice constants of the crystal.

FIG. 14 is a plan view of the prior-art X-ray diffraction apparatus for measuring precisely in-plane distribution of the interplanar spacing of the crystal lattice of a sample. This X-ray diffraction apparatus is disclosed in "X-ray Diffraction, Experimental Physics Course Vol. 20", edited by Kazutake Kohra, issued by Kyoritsu Shuppan, p. 477, 1988. This X-ray diffraction apparatus uses the double crystal method with which an X-ray diffraction rocking curve of a sample can be measured precisely. X-rays from an X-ray source 10 reflects at the first crystal 12, passes through the opening of a movable slit 14 and is then incident at a point P on a sample 28 which is the second crystal. The diffracted X-rays from the point P are detected by an X-ray detector 18 which may be, for example, a scintillation counter. The sample 28 is under ω-rotation within a small range of angle. The intensity of the diffracted X-rays is detected by the X-ray detector 18 during the sample rotation, so that the rocking curve of the aimed diffraction peak can be obtained. The rocking curve is defined as a peak profile of diffraction which may be illustrated in a graph with an incidence angle of X-rays to the sample on the abscissa and an intensity of the diffracted X-rays on the ordinate. The diffraction angle of the sample can be obtained from the rocking curve, and the interplanar spacing of the sample can be calculated by the diffraction angle.

When the movable slit 14 is translated in a direction perpendicular to the X-ray beam, the irradiation point is shifted to a point Q on the sample 28 so as to obtain another rocking curve at Q. The X-ray irradiation pointon the sample 28 can be thus altered by the translation of the movable slit 14 and therefore a plurality of the rocking curves for the respective points on the sample can be measured one after another. After all, in-plane distribution of the interplanar spacing can be obtained based on the resulting many rocking curves.

The prior-art X-ray diffraction apparatus mentioned above has the following drawbacks:

(1) It takes a very long time to measure many rocking curves for respective points on the sample (i.e., an area map measurement) because the rocking curves are to be measured one after another for different points. If the resulting area map should be used for process control of the deposition for a uniform composition, the area map measurement should be completed in a short time. The prior art apparatus however requires a too long time to do such a process control.

(2) The opening of the movable slit 14 is usually about 0.5 to 2.0 mm in width and about 5 to 10 mm in height. The size of the irradiated region on the sample 28 is nearly equal to the size of the opening of the movable slit 14 because the X-rays travel parallel to each other from the first crystal 12 to the sample 28. The intensity of diffracted X-rays from the sample 28 are detected by the X-ray detector 18, noting that the detected intensity is the sum of X-ray intensities diffracted from the all points within the above-sized irradiated region on the sample 28. The interplanar spacing derived from the resulting rocking curve is therefore an average value for the above-sized X-ray irradiated region on the sample 28. If it is intended to measure the interplanar spacing for a narrower region than the above-sized standard irradiated region, the opening of the movable slit should be smaller than the above size. For selecting one of various sizes of the irradiated region, many movable slits 14 of different opening sizes must be prepared.

(3) The movable slit 14 should be movable two-dimensionally in its plane for measuring the in-plane distribution of the interplanar spacing, requiring a moving mechanism for the movable slit 14. The use of the movable slit 14 may be replaced by the movement of the sample 28 in its plane., requiring, in such a case, a mechanism for moving the sample two-dimensionally in its plane.

(4) For obtaining in-plane distribution of the interplanar spacing, means for detecting a position at which X-rays are incident on the sample is required.

(5) If it is intended to irradiate only a certain small region, e.g., of about several tens micrometers on the sample, an X-ray beam should be narrowed by a slit. Moreover, the slit should be disposed as close to the sample as possible because any divergence angle of X-rays causes a blur of the irradiated region, hence requiring a special-designed slit.

(6) If it is intended to irradiate only a certain small region on the sample, the narrowed X-ray beam should be directed precisely to the small region with accuracy of about several micrometers. Therefore, positioning means such as a microscope is required and the moving mechanism for the movable slit or the sample should be of high accuracy. Besides, the positioning work is troublesome.

SUMMARY OF THE INVENTION

Accordingly it is an object of the invention to provide X-ray diffraction apparatus which can measure in-plane distribution of the interplanar spacing of the crystal lattice of a sample in a short time.

It is another object of the invention to provide X-ray diffraction apparatus which can measure in-plane distribution of the interplanar spacing without a moving mechanism for translating a slit or the sample.

X-ray diffraction apparatus according to the invention has a crystal collimator system which reflects X-rays which has only a predetermined wavelength out of the X-rays generated by an X-ray source. The reflected X-rays are incident on a sample. X-rays diffracted by the sample are detected by a two-dimensional position-sensitive X-ray detector. The sample is under rotation around an ω-axis which is parallel to the sample surface. X-ray intensities are detected and recorded at the same time for respective points of the detecting surface of the two-dimensional position-sensitive X-ray detector at every rotation angle of the sample with a predetermined pitch of angle, so that plural rocking curves can be measured at the same time for the respective points of the sample.

The crystal collimator system in the invention may have a single crystal plate or a plurality of crystal collimators combined with each other. The two-dimensional position-sensitive X-ray detector may be an X-ray CCD camera.

According to the invention, the two-dimensional position-sensitive X-ray detector is used for the precision measurement of lattice constants, so that a plurality of X-ray rocking curves can be measured at the same time for the respective points on the sample and an area map of the lattice constants of the sample can be obtained in a short time.

BRIEF DESCRIPTION OF THE DRAWINGS

FIG. 2 is a plan view of the X-ray diffraction apparatus shown in FIG. 1;

DETAILED DESCRIPTION OF THE PREFERRED EMBODIMENTS

Figure 1:
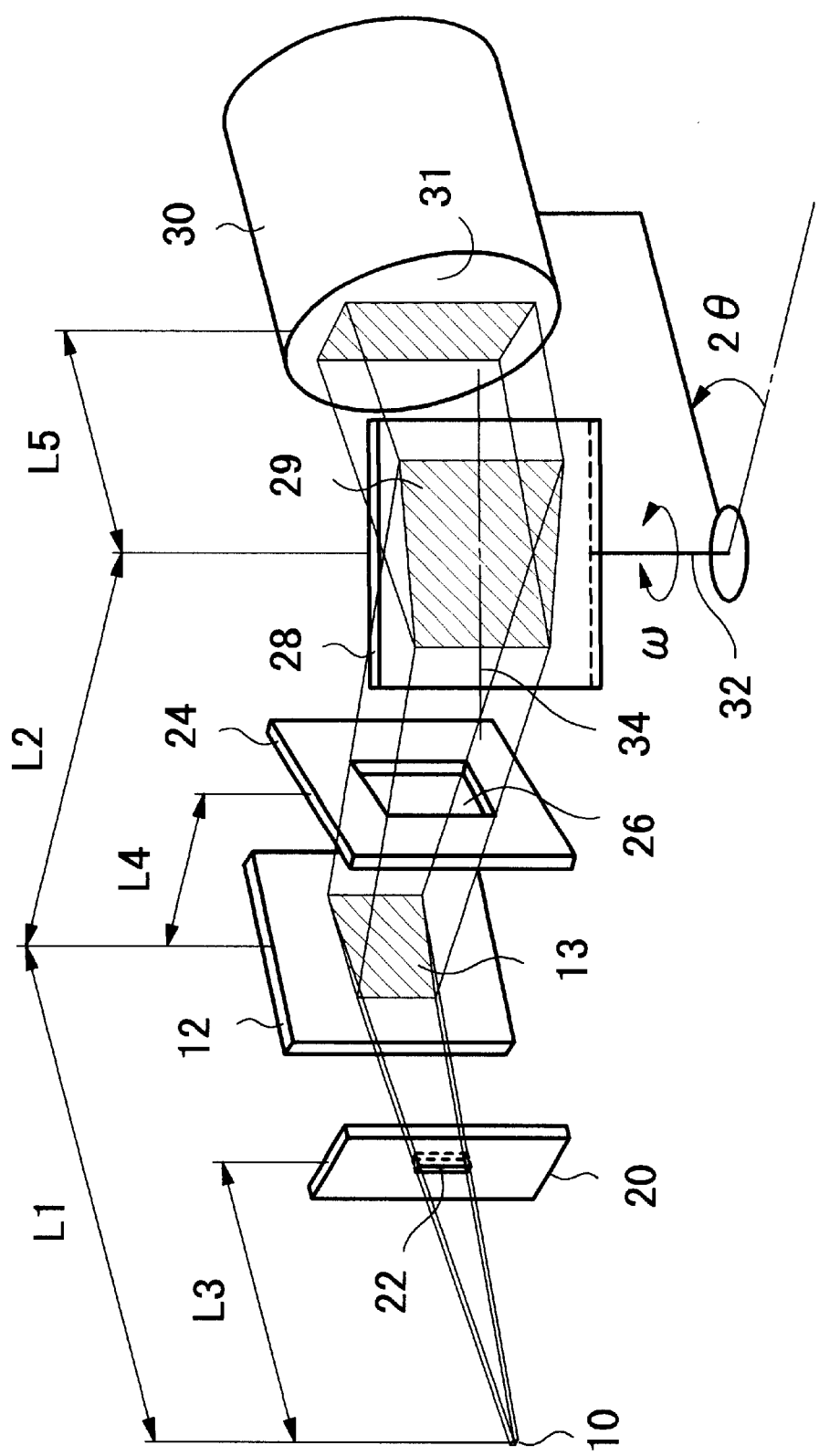
FIG. 1 is a perspective view showing the first embodiment of the invention.

In the following explanation, it is assumed that the measurement is directed to the interplanar spacing of the crystal lattice of an epitaxial thin film deposited on a GaAs (gallium arsenide) single crystal substrate. Referring to FIG. 1, X-rays emitted by an X-ray source 10 pass through the opening 22 of the first slit 20 and are then incident on the first crystal 12. The X-rays reflected by the first crystal 12 pass through the opening 26 of the second slit 24 and are then incident on a sample 28. The X-rays diffracted by the sample 28 are detected by a two-dimensional position-sensitive X-ray detector 30. The output of the X-ray detector 30 can be recorded by a recording device from which rocking curves can be derived.

The material of the target of the X-ray source 10 is copper and its characteristic X-rays CuKα is used for the measurement. The apparent focus size of the X-ray source 10 is 1 mm in width and 0.5 mm in height which corresponds to the ordinary size of the point focus taken out from the normal-focus X-ray tube.

The X-ray source 10 and the first slit 20 are separated by a distance L3 which is 550 mm. The opening 22 of the first slit 20 is 1 mm in width (which is equal to the width of the apparent focus size of the X-ray source) and H3 in height which is about 7 mm. The height H3 is determined with the sample size and the sensitive area of the X-ray detector in mind. The center of the first crystal 12 and the second slit 24 are separated by L4 which is 100 mm. The opening 26 of the second slit 24 is 10 mm in width and H4 in height which is about 9 mm.

The X-ray source 10 and the center of the first crystal 12 are separated by a distance L1 which is 650 mm. The material of the first crystal 12 may be a perfect crystal of Si (silicon) or Ge (germanium) Because the first crystal 12 has functions of both making the incident X-rays to the sample 28 monochromatic and making them parallel, the first crystal 12 thus being called as a crystal collimator. When the interplanar spacing of the first crystal 12 for reflection is close to the interplanar spacing of the sample to be measured, a good result would be expected with a high angular resolution. For example, where the GaAs (004) reflection is to be measured, it is preferable to use the Ge(004) reflection as the first crystal 12. In such a case, it becomes nearly the (+,−) parallel arrangement of the double crystal method, noting that on the contrary this invention may use a non-parallel arrangement.

The first crystal 12 utilizes asymmetric reflection which can make the incident X-ray beam to the sample broader. Referring to FIG. 2, when X-rays are incident at an incidence angle α, which is 5 degrees, on the surface of the first crystal 12, the reflected X-rays travel in a direction of 2 θm, which is 66 degrees, with respect to the direction of the incident X-rays. In this case, the Ge (004) plane of the first crystal 12 is inclined at 28 degrees to the surface of the crystal (i.e., the crystal 12 is so designed). When the width F of the incident X-ray beam to the first crystal 12 is 1 mm, the width, in a horizontal plane, of the reflected X-ray beam becomes 10 mm, i.e., the width of the reflected beam becomes 10 times that of the incident beam, so that a monochromatic, parallel and broader X-ray beam can be obtained.

Referring again to FIG. 1 for explanation of the vertical divergence of X-rays, X-rays from the X-ray source 10 divergent vertically and monotonously both before and after the reflection at the first crystal 12. The vertical divergence of X-rays is limited by the respective heights of the opening 22 of the first slit 20 and the opening 26 of the second slit 24. The heights of the openings 22, 26 are so selected, for example, that the irradiated region on the sample 28 may have a predetermined height (e.g., 10 mm). In this embodiment, the height H3 of the opening 22 is about 7 mm and the height H4 of the opening 26 is about 9 mm.

The center of the first crystal 12 and the center of the sample 28 are separated by a distance L2 which is 150 mm. The sample 28 is an epitaxial gallium-arsenic (Ga—As) series thin film deposited on a GaAs single crystal substrate. In this embodiment, an object of measurement is the diffraction peak of the GaAs(004) lattice plane which is parallel to the surface of the sample 28. The sample 28 is held on a sample holder which is rotatable around an ω-axis 32. With the ω-rotation, the incidence angle ω of X-rays to the surface of the sample 28 varies. The ω-axis extends vertically and thus parallel to the surface of the sample 28. The sample 28 can also be tilted around a χ-axis 34 which extends horizontally. With the χ-rotation, the tilt angle χ varies. When the ω-angle and the χ-angle are adjusted properly, the diffraction condition is satisfied and the diffracted X-rays come out from the X-ray irradiated region of the sample 28.

Referring to FIG. 2, X-rays coming from the first crystal 12 are incident at an incidence angle ω on the surface of the crystal 28. When the incidence angle ω becomes equal to a certain angle θ (=about 33 degrees) which satisfies the Bragg's law, the diffracted X-rays come out in a direction of 2 θ (=about 66 degrees) with respect to the direction of the incident X-rays. The sample 28 is rotated or scanned within a small range of angle around the ω-axis 32. Rocking curves can be measured with the scanning rotation.

Referring to FIG. 1, the center of the sample 28 and the detecting surface 31 of the X-ray detector 30 are separated by a distance L5 which is 50 mm. The X-ray detector 30 is a two-dimensional position-sensitive X-ray detector which is, in this embodiment, an X-ray CCD (charge coupled device) camera. With the X-ray detector 30, the intensities of the diffracted X-rays coming from the respective points on the sample 28 can be detected respectively at the same time. The X-ray detector 30 is rotatable around the ω-axis 32. With this rotation, the X-ray detector 30 can be adjusted in a direction facing toward the diffracted X-rays.

Figure 13:
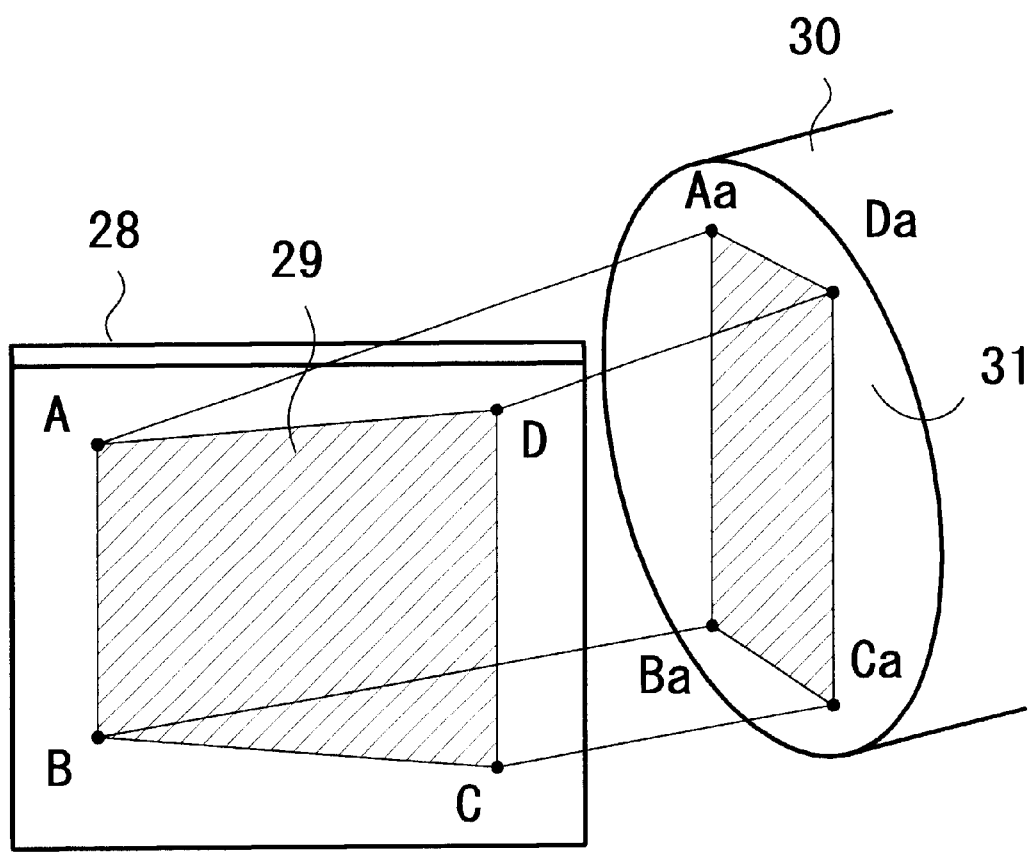
FIG. 13 is a perspective view showing a relationship between the X-ray irradiated region on the sample and the detecting points on the detecting surface of the X-ray detector.
Figure 14:
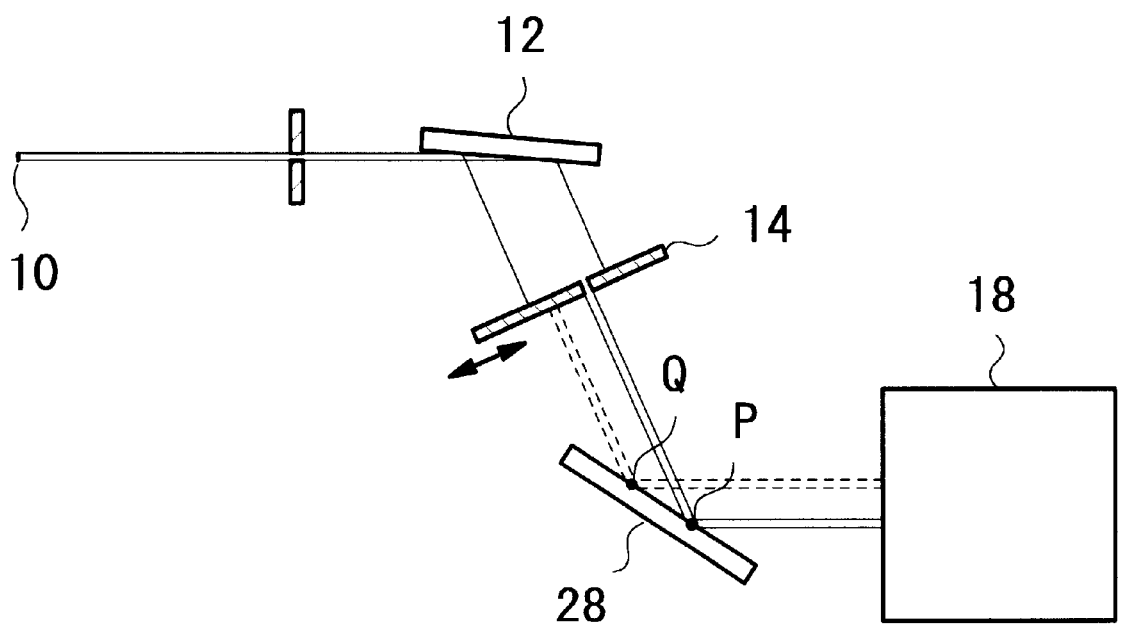
FIG. 14 is a plan view of the prior-art X-ray diffraction apparatus as discussed above for measuring precisely in-plane distribution of the interplanar spacing of the crystal lattice of a sample.

Next, the operation of the X-ray diffraction apparatus described above will be explained. Referring to FIG. 1, X-rays from the X-ray source 10 are limited by the first slit 20 and then incident on the first crystal 12. The X-ray irradiated region 13 is about 10 mm in width and about 8 mm in height. The reflected X-rays at the first crystal 12 pass through the second slit 24 and then are incident on the sample 28. The X-ray irradiated region 29 on the sample 28 is about 10 mm in width and about 10 mm in height. Referring to FIG. 13, the region 29 has a shape of nearly a rectangular having corners A, B, C and D. The diffracted X-rays from the irradiated region 29 are detected by the X-ray detector 30 in which each pixel of the detecting surface 31 can detect its intensity separately. Because the diffracted X-rays at the irradiated region 29 travel parallel to each other until they reach the detecting surface 31 of the X-ray detector 30, a point within the X-ray irradiated region 29 on the sample 28 and a point within the detecting surface of the X-ray detector 30 correspond to each other, i.e., one-to-one correspondence. Namely, the diffracted X-rays at the point A on the sample will reach a point Aa on the detecting surface 31 and similarly the diffracted X-rays at the points B, C and D will reach points Ba, Ca and Da respectively.

It is now assumed that the sample 28 is an epitaxial gallium-arsenic-phosphorus (Ga—As—P) series thin film deposited on a GaAs single crystal substrate and the ratio of As to P varies slightly with positions on the sample. That is, the interplanar spacing of the thin film varies slightly with positions on the sample. Such a sample 28 is scanned or rotated within a small range of the incidence angle ω around the Bragg angle θ (=33 degrees) so that the GaAs (004) plane may satisfy the diffraction condition. With this condition, the diffracted X-ray intensities from the sample 28 are detected so that each rocking curve of the diffraction peak of the epitaxial thin film can be measured at the same time for each pixel of the X-ray detector 30. Therefore, in this invention, many rocking curves for many points can be measured at the same time. While the prior-art apparatus requires many times of measurement during a scanning translation of the irradiated point on the sample, this invention can measure many rocking curves at the same time without any translation of a slit or a sample and thus with the reduced period of time. Theoretically, the most available number of the rocking curves with one scanning rotation is the number of the CCD pixels.

Figure 3A:
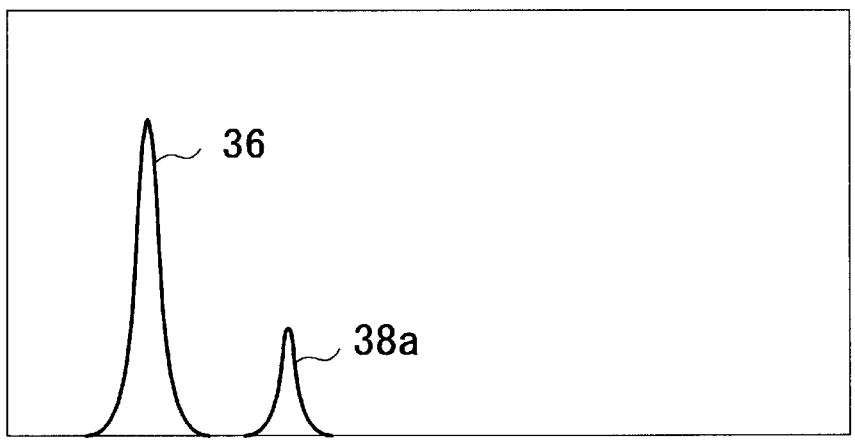
FIGS. 3A–3C are graphs indicating X-ray rocking curves.

FIG. 3A shows a rocking curve of the X-rays measured at the point Aa on the detecting surface 31, i.e., the X-rays diffracted at the point A on the sample. The ordinate represents an intensity of the diffracted X-rays and the abscissa represents a rotation angle ω of the sample. The diffraction peak 36 is the peak of GaAs (004) plane of the substrate. The lower peak 38a is the peak of the epitaxial thin film deposited on the substrate. As shown in the graph, if the diffraction peak 38a, which is the object of measurement, and the diffraction peak 36b of GaAs (004), which becomes the reference peak, are depicted in the same graph, the angle of the object peak 38a can be determined precisely with the reference of the angle of the substrate peak 36.

Figure 3B:
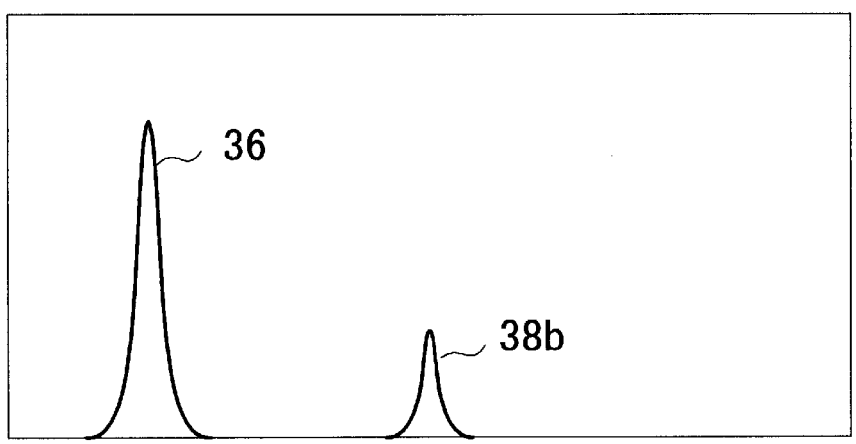

FIG. 3B shows a rocking curve of the X-rays measured at the point Ba on the detecting surface 31, i.e., the X-rays diffracted at the point B on the sample. The higher peak 36 is the peak of GaAs(004) plane of the substrate and it appears at the same angle as in FIG. 3A. On the contrary, the lower peak 38b is the peak of the epitaxial thin film and it appears at a slightly different angle from the peak 38a in FIG. 3A, because the composition of the epitaxial thin film varies slightly with the points A and B on the sample, which causes that the interplanar spacing varies slightly with the points A and B.

Figure 3C:
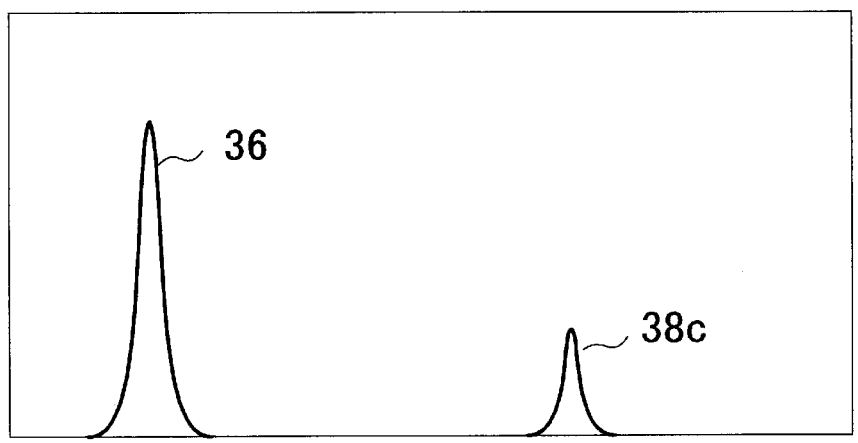

FIG. 3C shows a rocking curve of the X-rays measured at the point Ca on the detecting surface 31, i.e., the X-rays diffracted at the point C on the sample. The lower peak 38c appears also at a slightly different angle from the peak 38a in FIG. 3A.

Although FIGS. 3A–3C show only three rocking curves for the three points A, B and C, similar rocking curves can be obtained for the respective all pixels within the irradiated region of the detecting surface on which the diffracted X-rays impinge. On the basis of these rocking curves, diffraction angles for the respective points on the thin film deposited on the sample can be measured precisely. Further, on the basis of the diffraction angles, the interplanar spacing values for the respective points on the thin film can be calculated, then completing the area map of the interplanar spacing.

It is noted that if it is intended to measure the rocking curves within a narrower range of angle, the X-ray detector 30 may be stationary during the stepwise rotation of the sample 28 with a certain pitch of angle. On the contrary, if the sample 28 is rotated stepwise over several degrees as for the investigation of the superlattice, it is preferable to rotate the X-ray detector 30 with the sample 28. In this case, the pitch of the stepwise rotation of the X-ray detector 30 should be twice the pitch of the sample rotation.

The thus obtained area map data of the rocking curves is to be processed as described below. First, the distance distortion caused by the cosine effect which will be explained below is corrected and then the positions on the detecting surface is converted to the positions on the sample so that the relationship between the CCD pixels and the positions on the samples can be determined. Next, plural pixels may be combined and the X-ray intensities of the pixels may be averaged or integrated if necessary.

With the use of the sample having the selective growth region (i.e., a thin film is deposited epitaxially on only a certain region of the sample), the diffracted X-rays from the selective growth region can be observed in a topographic image in this invention. In this case, if the pixel position of the detector (which may be plural pixels) which corresponds to the selective growth region has been researched in advance and the X-ray intensity data of such a pixel will be plotted in a graph, the rocking curve of the selectively-grown material can be obtained easily.

For investigation of the thin film uniformity on a wafer, wide area measurement is required. In this case, it is preferable to make the beam width broader and to use a CCD camera having a larger size of aperture.

The information of the X-ray intensities taken by the CCD camera may become the X-ray intensities along the diffraction angle, i.e., the rocking curve, when giving attention to a certain point of the sample. On the other hand, the two-dimensional information of the X-ray intensities taken by the CCD camera may become an X-ray topographic image when giving attention to a certain angle of rotation of the sample. Therefore, this invention includes both the X-ray topography and the rocking curve measurement. In view of this, it may be said that this invention improves the X-ray topography, which has not been considered as the quantitative evaluation method, into the quantitative method.

Figure 7:
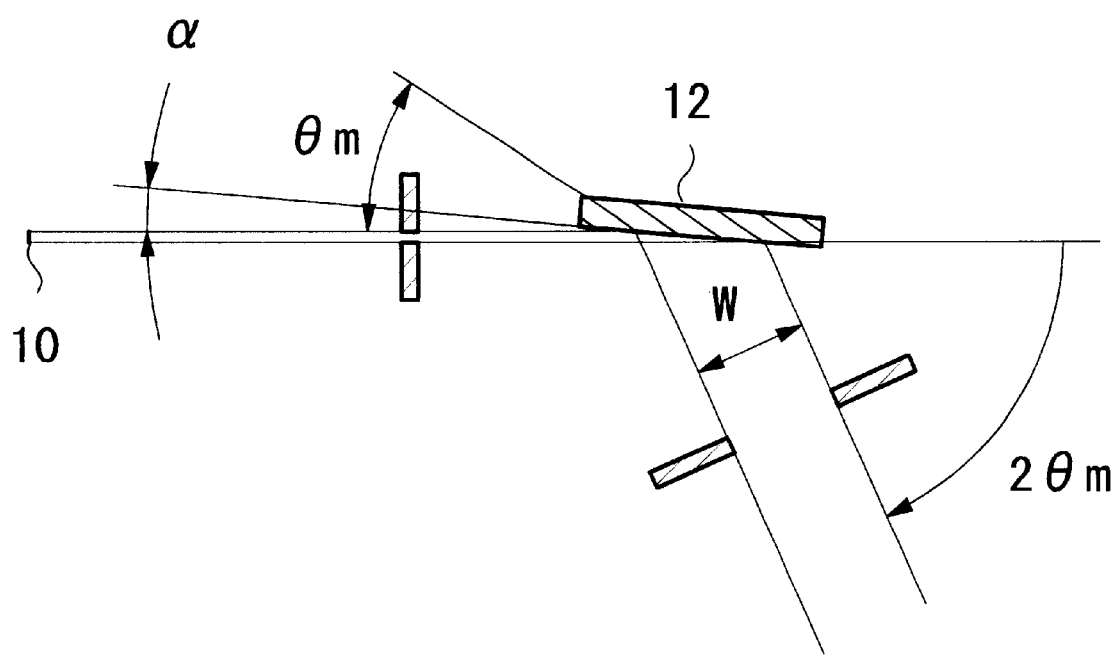
FIG. 7 is an enlarged plan view showing reflection by the first crystal.

Next, the X-ray diffraction apparatus will be explained with practical values. Referring to FIG. 7, the beam width W of the reflected X-rays at the first crystal 12 is given by the following equation:

$$W = F \sin(2\theta m - \alpha)/\sin\alpha$$

where, F is the apparent focus width of the X-ray source 10, $\theta m$ is the Bragg angle of the first crystal 12, and $\alpha$ is the X-ray incidence angle to the surface of the first crystal 12. Assuming that the characteristic X-rays to be used is CuK$\alpha$1 and the reflection plane of the first crystal 12 is Ge (004), 2$\theta m$ is about 66 degrees. When the first crystal 12 is so designed that the Ge (004) plane is inclined at 28 degrees to the crystal surface and X-rays are incident at an incidence angle $\alpha$ which is 5 degrees to the first crystal 12, the CuK$\alpha$1 rays can be reflected by the first crystal 12. When the apparent focus width F of the X-ray source 10 is 1 mm, the beam width of the reflected X-rays at the first crystal 12 becomes about 10 mm. Namely, the first crystal 12 using the asymmetric reflection makes the X-ray beam width about 10 times.

Referring next to FIG. 2, the width S of the X-ray irradiated region 28 on the sample 28 is given by the following equation:

$$S = W/\sin\omega$$

where, $\omega$ is the incidence angle to the surface of the crystal 28. When $\omega$ becomes equal to the Bragg angle $\theta$ which is about 33 degrees for a combination of GaAs(004) and CuK$\alpha$1, X-rays can be diffracted at the sample 28 and detected by the X-ray detectors 30. Substitution of W=10 mm and $\omega=\theta=33$ degrees in the equation gives S=about 18 mm.

Next, the width T of the X-ray image on the detecting surface 31 of the X-ray detector 30 is given by the following equation:

$$T = S\cos\phi = S\cos(90° - 2\theta + \omega)$$

where, the angle $\phi$ is as shown in FIG. 2. Substitution of $\omega=\theta=33$ degrees in the equation gives T=about 9.8 mm. Namely, the width S, which is about 18 mm, of the irradiated region on the sample is reduced by the cosine effect to the width T, which is about 9.8 mm, of the irradiated region on the detecting surface 31 of the X-ray detector.

Figure 4:
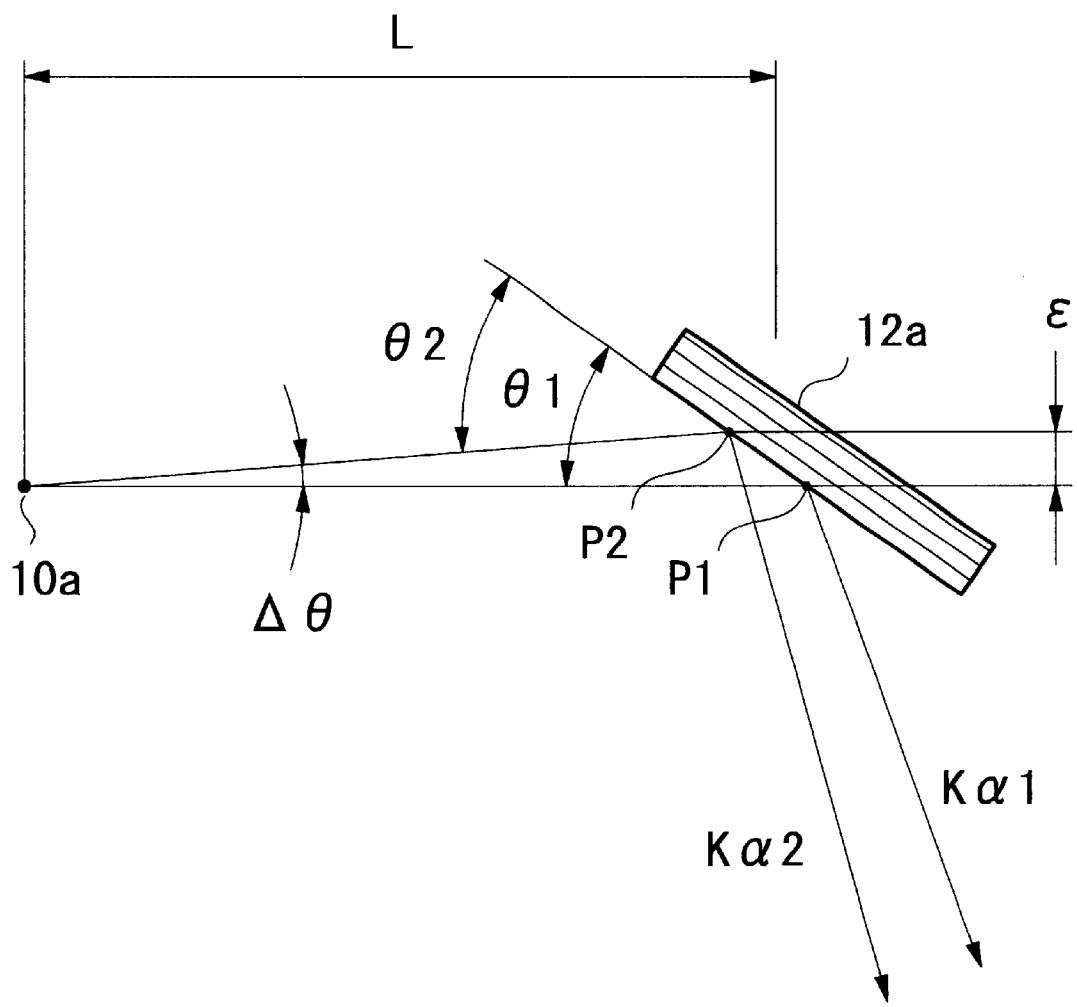
FIG. 4 is a plan view for explanation of the limited condition for the separation, by the first crystal, of the two characteristic X-rays.

Next, the separation of CuK$\alpha$1 rays and CuK$\alpha$2 rays will be explained. FIG. 4 is a plan view for explanation of the limited condition for the separation of CuK$\alpha$1 rays and CuK$\alpha$2 rays at the first crystal 12a. It is assumed here that an X-ray source 10a has an ideal point focus, i.e., an apparent focus width is zero. X-rays from the X-ray source 10a are incident on the first crystal 12a. The CuK$\alpha$1 rays can satisfy the Bragg's law with an incidence angle $\theta$1 and thus can be diffracted at a point P1 on the first crystal 12a. On the other hand, the CuK$\alpha$2 rays can satisfy the Bragg's law with another incidence angle $\theta$2 and thus can be diffracted at another point P2 on the first crystal 12a. Hence the two characteristic X-rays will satisfy the Bragg's law at different points on the first crystal 12a. If it is intended that only the CuK$\alpha$1 rays can be reflected but the CuK$\alpha$2 rays can not be reflected, the incidence line of the CuK$\alpha$2 rays should be cut by the first slit.

On the other hand, the width of the opening of the first slit has been determined beforehand as described below. Because the actual X-ray source 10a has a finite width F, it is preferable that the width of the first slit is approximately equal to the width of the X-ray source 10a for utilizing X-rays as much as possible.

Considering the limited condition for the separation of the two characteristic X-rays in these circumstances, the separation width $\epsilon$ at the first slit 12a should be larger than the width (which may be equal to F) of the opening of the first slit. Hence the following equation is obtained.

$$\epsilon = L\Delta\theta > F$$

where, $\Delta\theta$ is the difference between $\theta$1 and $\theta$2. When the reflection plane of the first slit 12a is Ge(004), $\theta$1 is 32.91 degrees and $\theta$2 is 33.01 degrees. Substitution of F=1 mm in the equation gives L>573 mm. Hence in this embodiment L1 shown in FIG. 1 is set 650 mm with some margin. Because L1 is set long as described above, only the CuK$\alpha$1 rays can reflect at the first crystal. Although this explanation is for the symmetric reflection, the explanation may be applicable for the asymmetric reflection too.

Figure 5:
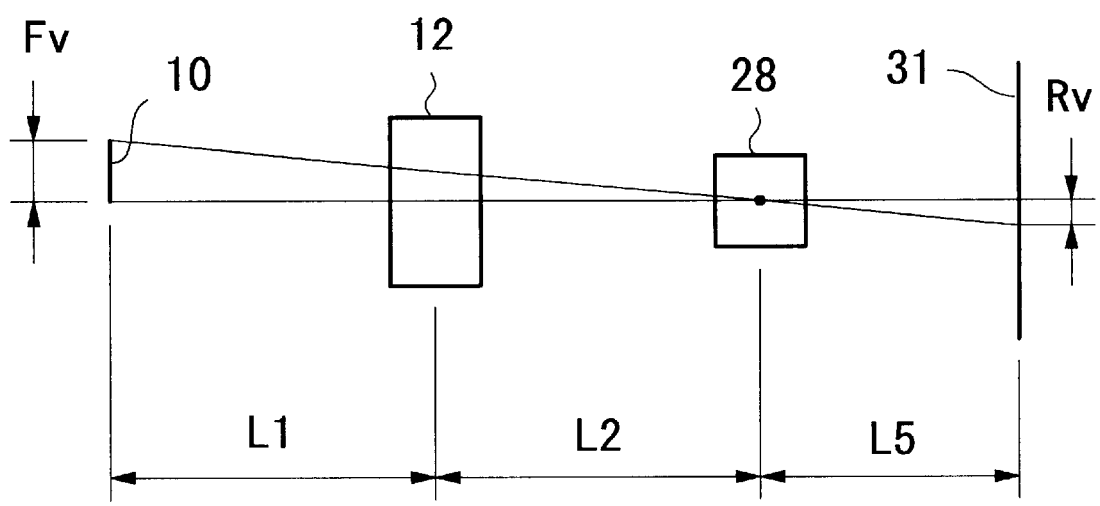
FIG. 5 is a front view for explanation of the vertical resolution of the X-ray diffraction apparatus.

Next, the resolution of the X-ray diffraction apparatus will be explained. The space resolution is important in this invention because the apparatus according to the invention can measure the area map of the interplanar spacing for respective points on the sample. FIG. 5 is a front view for explanation of the vertical resolution. The vertical resolution depends on the height Fv of the focal spot of the X-ray source 10, the vertical resolution being so-called a geometrical blur. Because the focal spot of the X-ray source 10 has a finite height, information coming from one point on the sample will have a height Rv on the detecting surface 31. This will be explained in detail below. The vertical divergence of X-rays will not depend on the first crystal 12 nor the sample 28 as previously described. Therefore, as shown in FIG. 5, the apparent height Fv of the focal spot of the X-ray source 10 becomes the image having a height Rv on the detecting surface 31 of the X-ray detector after reflection at a certain point on the sample 28. Rv is given by the following equation.

$$Rv = Fv\ L5/(L1+L2)$$

Substitution of Fv=0.5 mm, L5=50 mm, L1=650 mm and L2=150 mm in the equation gives that Rv becomes about 30 micrometers. Therefore, the vertical resolution on the detecting surface, which is caused by the apparent focus size of the X-ray source, is about 30 micrometers.

Figure 6:
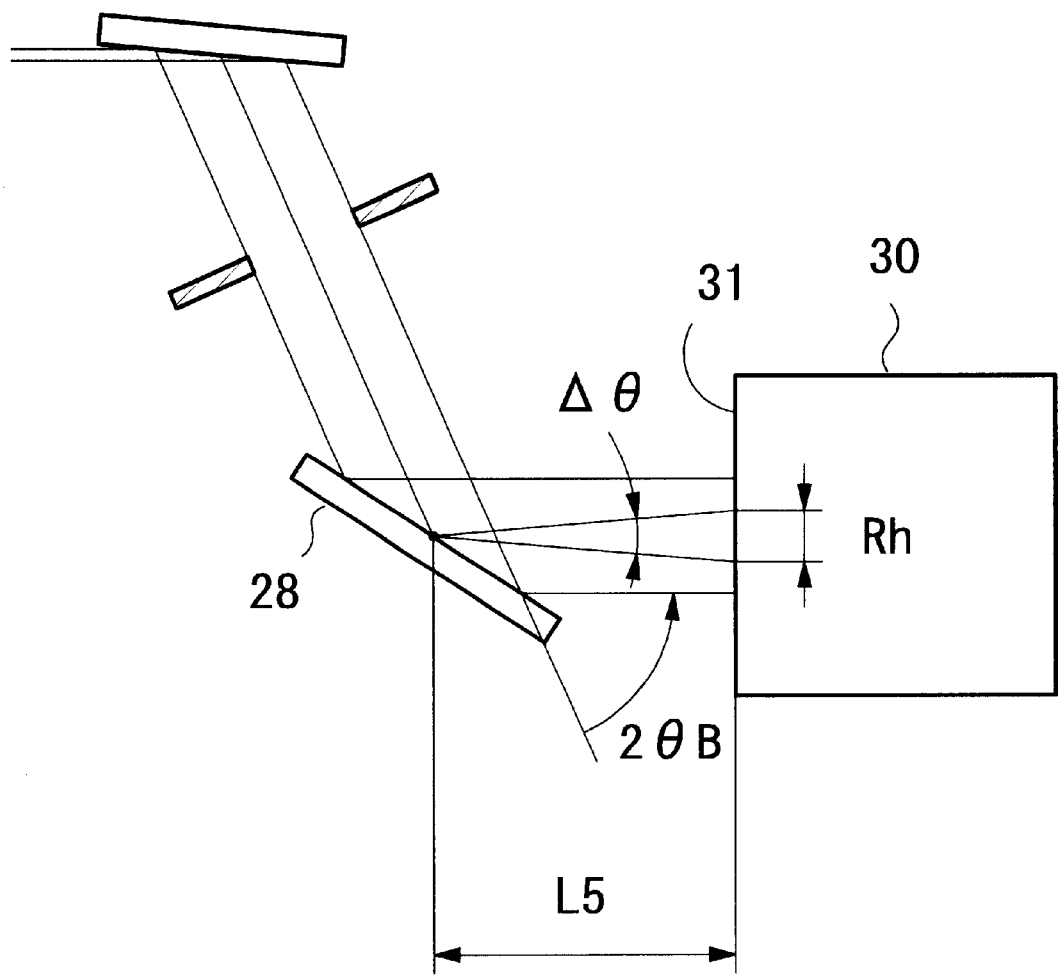
FIG. 6 is a plan view for explanation of the horizontal resolution of the X-ray diffraction apparatus.

Next, the horizontal resolution will be explained. FIG. 6 is a plan view for explanation of the horizontal resolution. The horizontal resolution does not depend on the focus size of the X-ray source but is caused by the wavelength dispersion of CuKα1. This will be explained in detail below. The X-rays diffracted at a certain point on the sample 28 are divergent to the width Rh on the detecting surface 31 of the X-ray detector 30 under the influence of the wavelength dispersion of CuKα1. Rh is given by the following equation.

$$Rh = L5\ \Delta\theta = L5(\Delta\lambda/\lambda)\tan\theta B$$

where, $(\Delta\lambda/\lambda)$ represents the wavelength dispersion of CuKα1, its value being $3.8\times10^{-4}$. θB is the Bragg angle, which is 33 degrees, of the GaAs(004) plane of the sample substrate. L5 is 50 mm. Substitution of these values in the equation gives that Rh becomes about 12 micrometers.

It will be understood from the explanation above that both the vertical and horizontal resolution can be improved more as the distance L5 is smaller (i.e., as the X-ray detector 30 is located more close to the sample 28).

Figure 8:
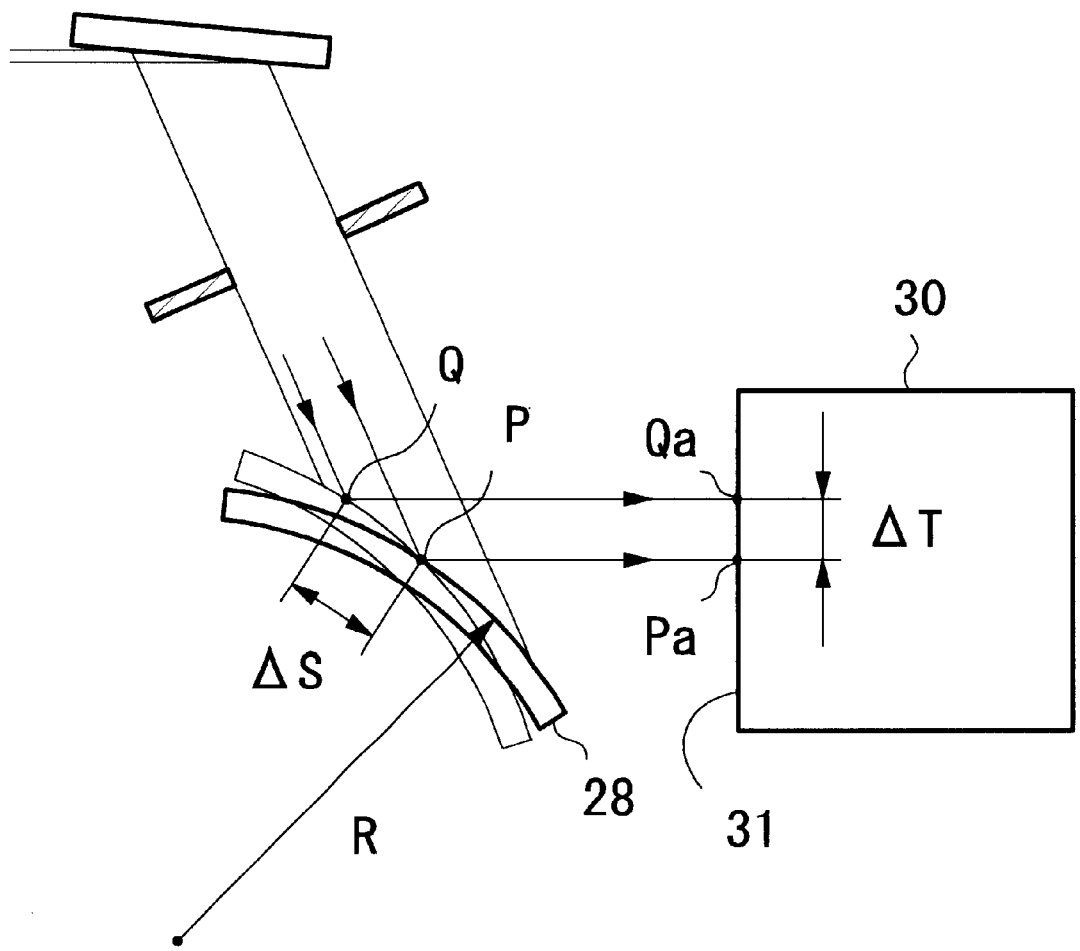
FIG. 8 is a plan view showing a case having a sample crystal with a bend.

Referring next to FIG. 8, there will be explained the case that a sample crystal has a bend. When the sample crystal has a bend whose radius of curvature is represented by R, the incidence angle of X-rays to the crystal lattice plane depends on a position on the sample 28. Therefore, when the sample 28 is under rotation, only a small area around a certain point within the irradiated region on the sample will satisfy the Bragg's law. It is assumed here that the sample surface has a convex curvature. When the sample 28 is under rotation and reaches a certain angle, only a small area around the point P on the sample 28 will satisfy the Bragg's law. Any other point will not satisfy the Bragg's law. The diffracted X-rays from the area around the point P may reach the point Pa on the detecting surface 31 of the X-ray detector 30. When the sample 28 is further rotated by Δω around the ω-axis, only an area around another point Q on the sample 28 will satisfy the Bragg's law. The diffracted X-rays at the area around the point Q may reach the point Qa on the detecting surface 31 of the X-ray detector 30. The distance between the point P before the Δω rotation and the point Q after the Δω rotation is represented by ΔS. It is noted in FIGS. 8 and 9 that the bend of the sample is exaggeratingly illustrated for easy understanding.

Figure 9:
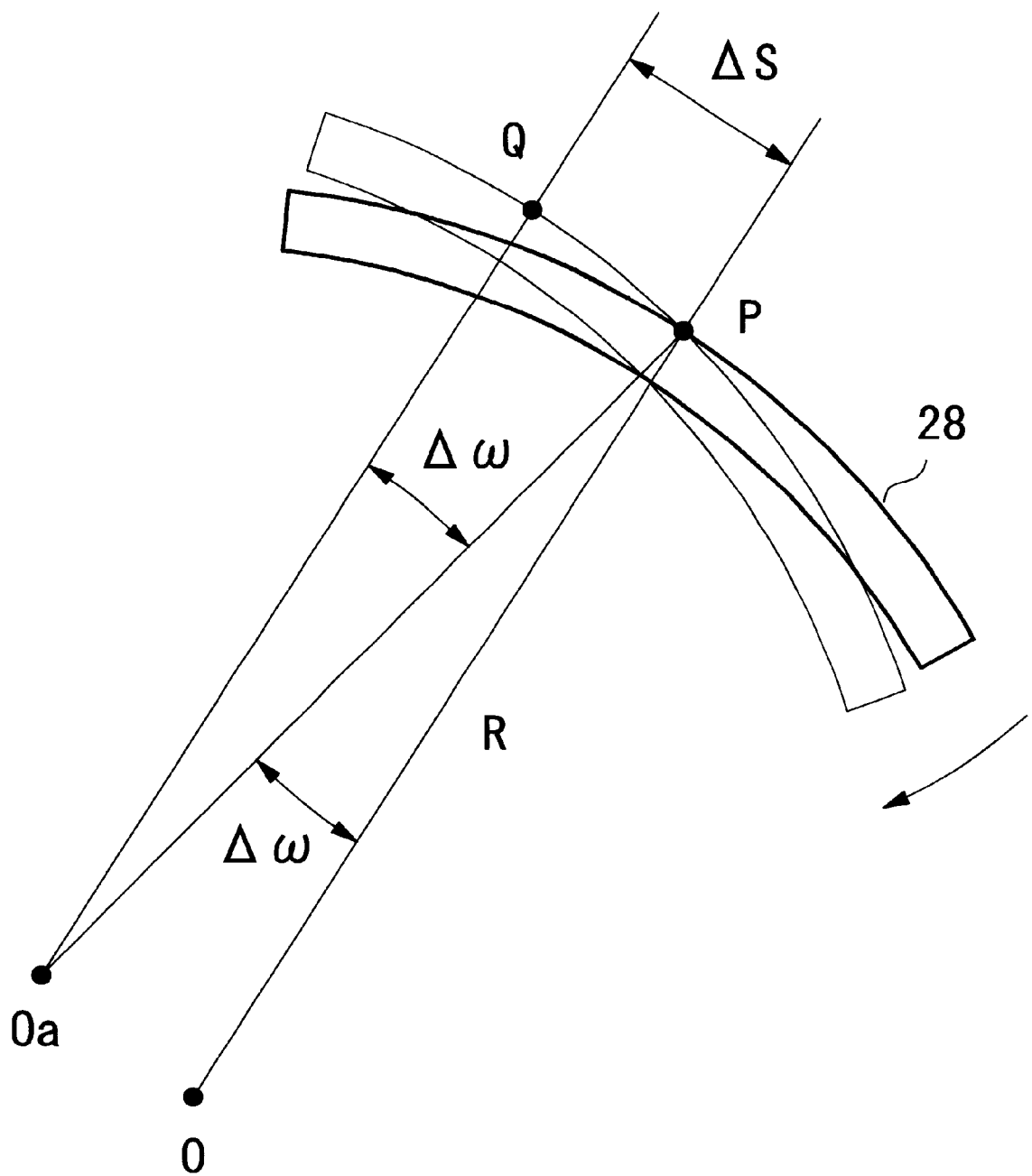
FIG. 9 is an enlarged view of the vicinity of the sample shown in FIG. 8.

With the X-ray diffraction apparatus according to the invention, the radius of curvature of the sample crystal can be measured based on AS mentioned above. Referring to FIG. 9 which is an enlarged view of the vicinity of the sample shown in FIG. 8, the radius of curvature of the sample 28 is represented by R and the center of curvature is the point O. In one condtion, the point P on the sample will satisfy the Bragg's law, and in another condition after the Δω rotation of the sample, the point Q will satisfy the Bragg's law. Assuming that the sample 28 would be rotated by Δω around the point P, the center of curvature of the sample will be shifted from the point O to the Point Oa. Because the X-ray incidence angle at the point P before the Δω rotation and the X-ray incidence angle at the point Q after the Δω rotation are equal, a line passing through the points O and P and another line passing through the points Oa and Q are parallel to each other. Therefore, the angle between the line passing through the points Oa and P and the line passing through the points Oa and Q is equal to Δω. Hence the radius of curvature is given by the following equation.

$$R = \Delta S/\Delta\omega$$

ΔS is readily calculated, as shown in FIG. 8, from the distance ΔT between the point Pa and the point Qa on the surface 31 of the X-ray detector 30. After all, if the sample having a bend is rotated by Δω and the detecting points Pa and Qa of the diffracted X-rays before and after the Δω rotation are observed, the radius of curvature of the sample crystal can be obtained. Furthermore, whether the bent is convex or concave can be seen from whether the point Q after the rotation is shifted to the left or the right from the point P.

Figure 10:
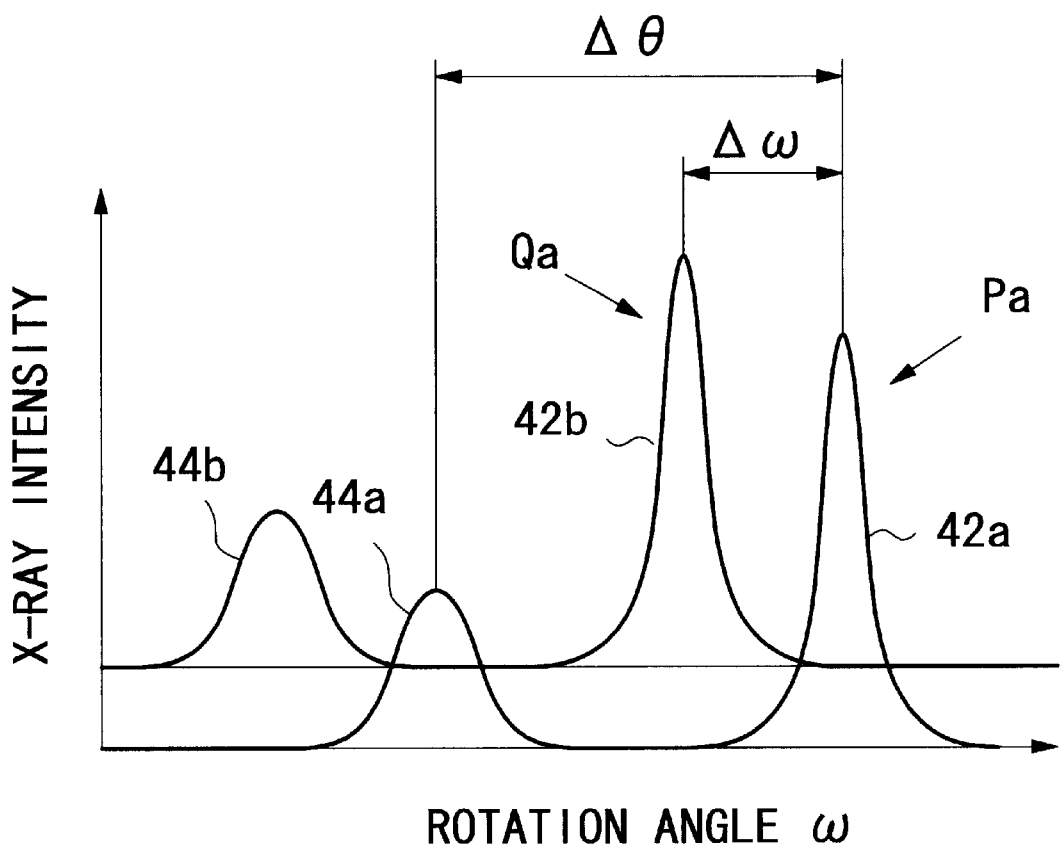
FIG. 10 is a graph showing rocking curves which are measured at two points on the detecting surface of the X-ray detector.

By the way, where it is intended to do the precision measurement of the interplanar spacing of the epitaxial thin film on a single crystal substrate, the resulting interplanar spacing might have an error under the influence of the bent of the single crystal substrate. However, it is no problem as described below. FIG. 10 is a graph explanatorily showing rocking curves measured at the two points Pa and Qa on the detecting surface of the X-ray detector. In the rocking curve at the point Pa, the diffraction peak 42a of the single crystal substrate and the diffraction peak 44a of the epitaxial thin film on the substrate appear. On the other hand in the rocking curve at the point Qa, the diffraction peak 42b of the single crystal substrate and the diffraction peak 44b of the epitaxial thin film on the substrate appear. If the single crystal substrate would have no bend, the diffraction peaks 42a and 42b would appear at the same diffraction angle. The two peaks 42a and 42b actually appear, however, at the different diffraction angles with the difference Δω because of the bend of the substrate. It is important that the diffraction angles of the diffraction peaks 44a and 44b of the epitaxial thin film can be measured as the deviation Δθ from the reference peaks 42a and 42b which are the diffraction peaks of the substrate, because the epitaxial thin film would have the same bend as the single crystal substrate. Therefore, the precision measurement of the interplanar spacing of the epitaxial thin film can be done without the influence of the bend of the substrate.

The phenomenon in which the diffraction peaks of the substrate measured at different points on the detecting surface appear at different diffraction angles may appear due to other reasons than the bend of the substrate. For example, a magnesia (MgO) substrate may consist of some domains of slightly different orientation. In another case, α-$Al_2O_3$ and $SrTiO_3$ substrates may have orientation continuously varying with positions along its surface, so-called a linage structure. In a further case using the double crystal method with a non-parallel arrangement, there is a slight difference in Bragg angle between around the vertical center and the upper and lower regions. Although there may be various reasons as described above in which the diffraction peak angle of the substrate crystal depends upon positions on the sample, the diffraction peak angle of the epitaxial thin film on the substrate can be precisely determined with the reference of the diffraction peak angle of the substrate crystal.

Figure 11:
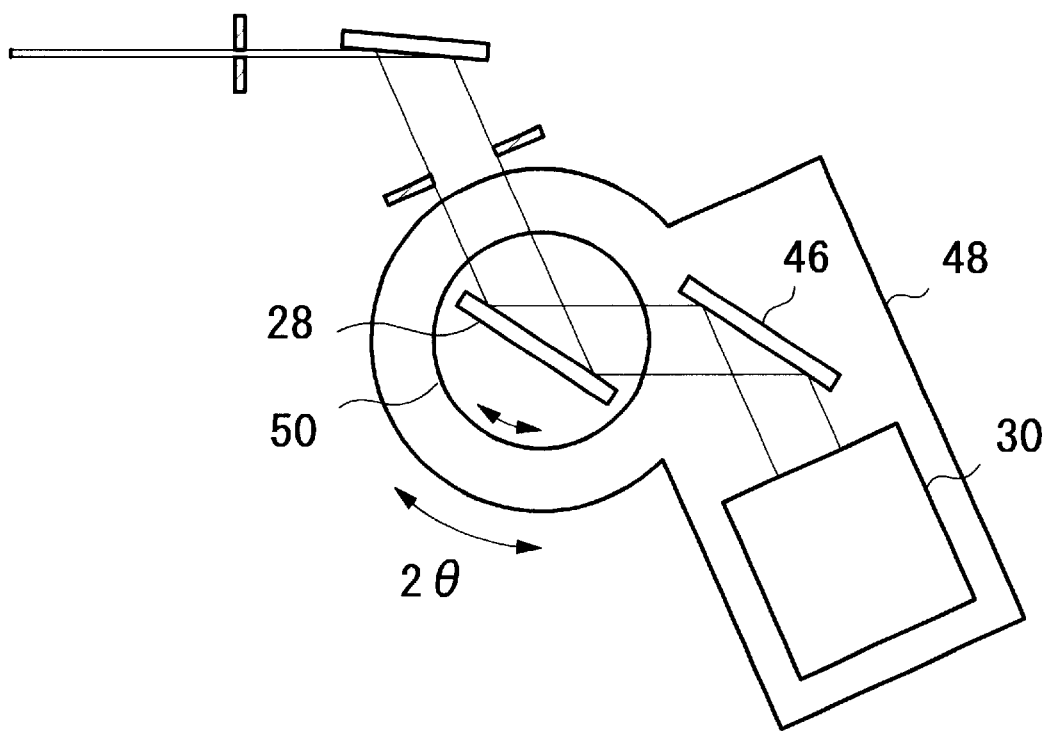
FIG. 11 is a plan view showing the second embodiment of the invention.

Next, the second embodiment according to the invention will be described with referring to FIG. 11. In this embodiment, an analyzer crystal 46 is arranged between the sample 28 and the X-ray detector 30. The analyzer crystal 46 and the X-ray detector 30 are mounted on a 2 θ-rotation plate 48 while the sample 28 is mounted on an ω-rotation plate 50. The diffracted X-rays from the sample 28 reflect at the analyzer crystal 46 and then detected by the two-dimensional position-sensitive X-ray detector 30. The analyzer crystal 46 makes possible to observe separately the deviation of the lattice constants (i.e., lattice distortion) and the deviation of the orientation. The resulting data is expressed usually as an intensity map in reciprocal lattice space. Because the measurement of such an intensity map requires many steps of scanning, it will take one to ten hours to obtain only one set of data. Therefore, with the prior-art apparatus, it will take a very long period of time to obtain an area map of the intensity map in reciprocal lattice space. On the contrary, with the use of the two-dimensional position-sensitive X-ray detector as in the invention, such an area map can be made by obtaining one set of data.

Figure 12:
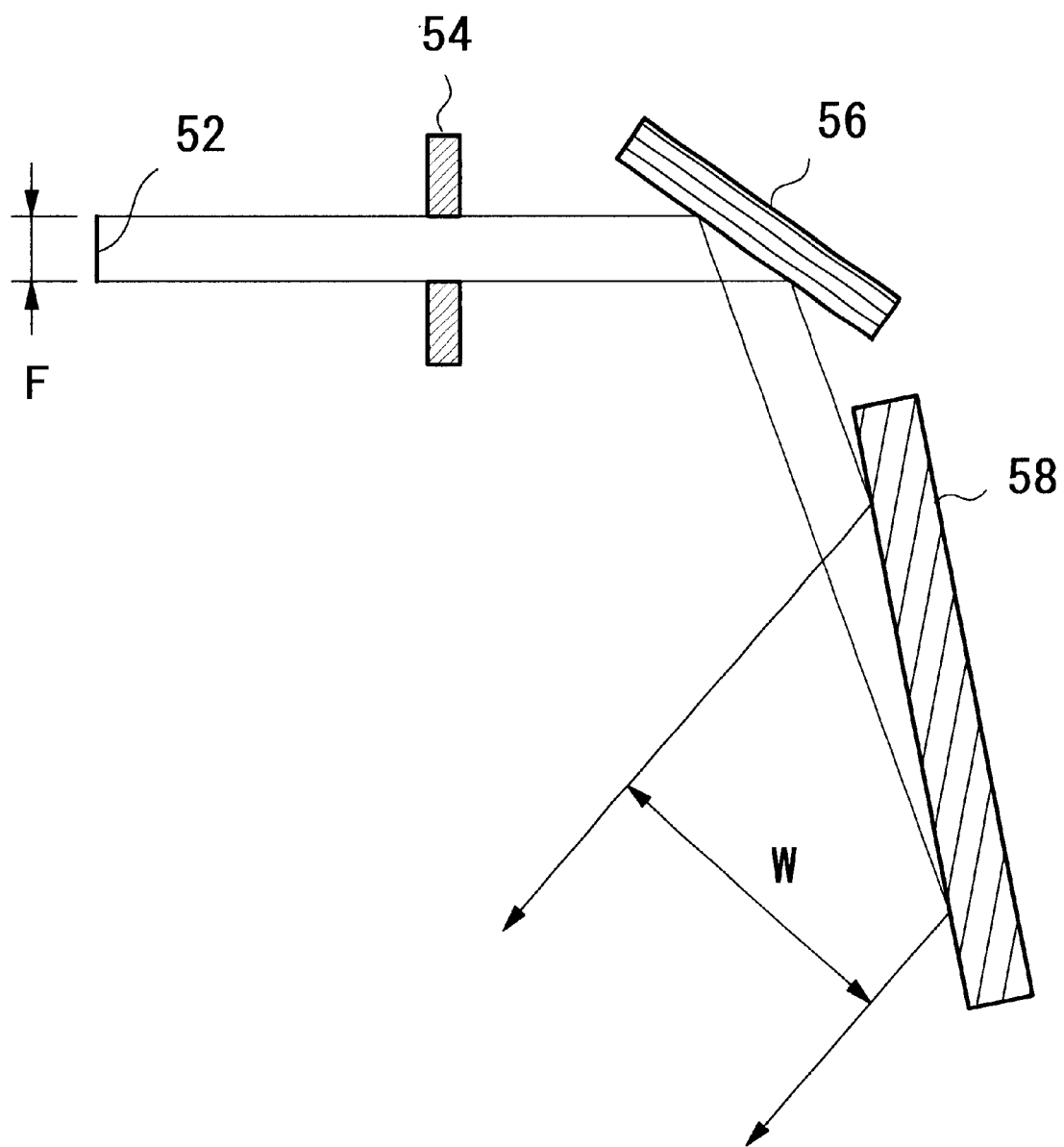
FIG. 12 is a plan view showing an X-ray source and a crystal collimator system in the third embodiment of the invention.

Referring to FIG. 12, it shows an X-ray source 52 and a crystal collimator system 56, 58 of the third embodiment according to this invention, other parts being basically identical with the first embodiment. In the third embodiment, the line-focus X-ray source 52 is used to irradiate a sample with a broader X-ray beam. The line-focus X-ray source 52 has an apparent focus size usually of 10 mm in width F and 0.05 mm in height. In the case of using such a line-focus X-ray source, it is important to remove K$\alpha$2, which is easily removed with the use of a crystal collimator system having double crystals 56, 58 of (+,+) arrangement. X-rays from the line-focus X-ray source 52 pass through the first slit 54 and then incident on the first crystal collimator 56 which is for symmetric reflection. The reflected X-rays at the first crystal collimator 56 are further reflected at the second crystal collimator 58 so as to have a broader beam width W. The second crystal collimator 58 is for asymmetric reflection so that an X-ray beam which is 10 mm in width is converted to a broader X-ray beam which is 50 mm in width. With the use of such a crystal collimator system, it would be possible to obtain a broader X-ray beam which can cover, for example, all regions of a wafer with a size of 2 to 3 inches. If it is disagreeable that the direction of the X-ray beam is altered to another direction due to the (+,+) arrangement, a channel-cut crystal may be used in place of such a crystal collimator system. Further, a four-crystal monochrocollimator may be used.

Next, the two-dimensional position-sensitive X-ray detector will be described. The X-ray CCD camera has recently be developed rapidly and is usable as the two-dimensional position-sensitive X-ray detector in this invention. Although there are some types of the X-ray CCD camera, the one used in the embodiments described above is a type in which X-rays are detected directly by CCD devices. This type is of high efficiency and its resolution is equal to a pixel size. The CCD camera may have a detecting surface with a size of about 10 to 20 mm times 10 to 20 mm and a pixel size of 12 or 24 micrometers. 512 or 1024 pixels of such a size may be arrayed both vertically and horizontally to form a detecting surface. Such a CCD device is usually cooled by liquid nitrogen or an electronic cooling system utilizing the Peltier effect. With the cooling means, inter-pixel oozing of electric charges will not occur during data storage with time so that a dynamic range of about four figures can be guaranteed.

Where a wide detecting surface is required, an X-ray image may be converted to a light image with the use of a fluorescent screen and the light image may be then incident on a CCD through a taper-type fiber system which has a wide inlet and a narrow outlet. The light image may be reduced by lens means so as to be detected by the CCD.

There can be used in the invention other types of the two-dimensional position-sensitive detector than the X-ray CCD. Such a detector may be one using amorphous Se or amorphous Si, a micro strip gas chamber (MSGC) or a multi-wire proportional counter (MWPC). Further, a combination of an X-ray image intensifier and a CCD television system may be used. In this case, the CCD will function not in the storage mode but in the television-rate mode. An ordinary high-sensitive X-ray television camera might be used although it has a poor dynamic range. The high-sensitive X-ray television camera might be used in the field in which it is enough to obtain only the diffraction peak angle with a high speed.

Further, an imaging plate (storage type phosphor) or an X-ray film might be used in principle in the invention although they can not make real-time detection of X-ray intensities.

Measurement of the in-plane distribution of the interplanar spacing of the crystal lattice of a sample may be applied for various fields as mentioned below.

(1) In the gallium-arsenic-phosphorus (Ga—As—P) series compound semiconductor, the composition and the interplanar spacing will satisfy the specific relationship. Therefore, the precise measurement of the interplanar spacing makes possible to obtain a ratio of As to P. With the use of the relationship for the Ga—As—P series compound semiconductor thin film deposited on a substrate, the measurement of the in-plane distribution of the interplanar spacing makes possible to obtain in-plane distribution of the composition and to evaluate the uniformity of the composition.

(2) There is a known technique in which many epitaxial thin films of different compositions are deposited on a common single crystal substrate at different positions on the substrate so as to efficiently search various functional materials. In this case, the measurement of the in-plane distribution of the interplanar spacing of the thin films on the common substrate can make possible to obtain the respective interplanar spacings of the different epitaxial thin films.

(3) In the production of semiconductor devices, there is a case that information on a selective growth region or a certain device region is required. In this case, it may be necessary to obtain information on only a limited region as of several tens to several hundreds micrometers in width and length. This invention can satisfactorily be used in that case in a manner that information on the object region can be obtained without the operation of narrowing an X-ray beam and aiming it only at the object region but with the operation only of taking out X-ray intensity information on a certain region on the detecting surface of the two-dimensional position-sensitive X-ray detector.

What is claimed is:

1. An X-ray diffraction apparatus comprising:

(a) an X-ray source;

(b) a sample holder for holding a sample having a surface, said sample holder being rotatable around an $\omega$-axis which is parallel to the surface of said sample;

(c) a crystal collimator system for reflecting, towards said sample, X-rays having a predetermined wavelength out of X-rays generated by said X-ray source;

(d) a two-dimensional position-sensitive X-ray detector having a detecting surface for detecting diffracted X-rays from said sample; and (e) means for simultaneously recording X-ray intensities detected at respective points on said detecting surface of said X-ray detector at rotation angles with a predetermined pitch of angle during rotation of the sample around said $\omega$-axis, to thereby obtain rocking curves for said respective points.

2. X-ray diffraction apparatus according to claim 1, wherein said X-ray detector comprises an X-ray CCD camera.

3. X-ray diffraction apparatus according to claim 1, wherein said crystal collimator system effects asymmetric reflection so that a width of an X-ray beam which is reflected by said crystal collimator system can be larger than a width of an X-ray beam which is incident on said crystal collimator system.

4. X-ray diffraction apparatus according to claim 1, wherein said X-ray detector is rotatable around said $\omega$-axis.

5. X-ray diffraction apparatus according to claim 1, wherein an X-ray irradiated region on said sample has an approximately rectangular shape.

6. X-ray diffraction apparatus according to claim 1, wherein an analyzer crystal is arranged between said sample and said X-ray detector.

7. X-ray diffraction apparatus according to claim 1, wherein said crystal collimator system comprises a plurality of crystal collimators.

8. X-ray diffraction apparatus according to claim 7, wherein said crystal collimator system comprises a symmetric-reflection crystal collimator and an asymmetric-reflection crystal collimator which are set in (+,+) arrangement.

9. A method for measuring X-ray rocking curves comprising:

(a) reflecting X-rays having a predetermined wavelength out of X-rays generated by an X-ray source by using a crystal collimator system;

(b) irradiating a sample with X-rays which are reflected by said crystal collimator system;

(c) rotating said sample around a $\omega$-axis which is parallel to a surface of said sample;

(d) detecting intensities of diffracted X-rays from said sample using a detecting surface of an X-ray detector; and (e) simultaneously recording X-ray intensities detected at respective points on the detecting surface of the X-ray detector at rotation angles with a predetermined pitch of angle during rotation of said sample around said $\omega$-axis, to thereby obtain rocking curves for said respective points.

10. A method according to claim 9, wherein said sample comprises at least one epitaxial thin film deposited on a single crystal substrate.

11. A method according to claim 9, further comprising taking out, as two-dimensional X-ray intensity information, detected X-ray intensities for respective points on said detecting surface of said X-ray detector at a certain angle of rotation of said sample around said $\omega$-axis, to thereby obtain an X-ray topographic image of said sample.

\* \* \* \* \*